United States Patent [19]

Ullman et al.

[11] Patent Number: 5,512,659
[45] Date of Patent: Apr. 30, 1996

[54] COMPOSITIONS USEFUL IN HETEROGENEOUS IMMUNOASSAYS

[75] Inventors: Edwin F. Ullman, Atherton; Hriar Kirakossian, San Jose; Mary C. Ericson, Santa Cruz; Richard P. Watts, Brisbane, all of Calif.

[73] Assignee: Syntex (U.S.A.) Inc., Palo Alto, Calif.

[21] Appl. No.: 389,659

[22] Filed: Aug. 4, 1989

[51] Int. Cl.⁶ .................. C07K 16/00; G01N 33/533; G01N 33/53
[52] U.S. Cl. .................. 530/391.1; 530/391.3; 530/391.5; 530/391.7; 530/391.9; 436/546; 436/800; 435/7.1; 435/7.92; 435/7.94
[58] Field of Search .................. 435/7, 177, 188, 435/7.1, 7.92, 7.94; 436/512, 513, 546, 800; 426/518, 536, 540; 530/387.1, 387.2, 388.1, 388.22, 388.9, 389.1, 391, 391.3–391.7, 802

[56] References Cited

U.S. PATENT DOCUMENTS

| | | |
|---|---|---|
| 4,223,237 | 10/1980 | Hevey et al. . |
| 4,298,685 | 11/1981 | Parikh et al. . |
| 4,420,568 | 12/1983 | Wang et al. ............... 436/536 |
| 4,476,229 | 10/1984 | Fino et al. ................ 436/500 |
| 4,659,678 | 4/1987 | Forrest et al. ............. 436/512 |
| 4,777,145 | 10/1988 | Luotola et al. . |
| 4,780,423 | 10/1988 | Bluestein et al. . |
| 4,904,583 | 2/1990 | Mapes et al. .............. 435/7.92 |

FOREIGN PATENT DOCUMENTS

| | | |
|---|---|---|
| 005271 | 11/1079 | European Pat. Off. . |
| 0160900 | 11/1985 | European Pat. Off. . |
| 0177191 | 4/1986 | European Pat. Off. . |
| 201079 | 11/1986 | European Pat. Off. . |
| 0201079 | 12/1986 | European Pat. Off. . |
| 2523311 | 9/1983 | France . |
| 2084317A | 4/1982 | United Kingdom . |

OTHER PUBLICATIONS

Babashak, et al. *Journal of Chromatography*, vol. 444 (1988). pp. 21–28.

Neurath, et al., Methods of Enzymology, vol. 73, part B: (J. J. Langone and H. Van Vunakis, editors), pp. 127–138, (1981) "Labeling of Antigens and Antibodies".

*Primary Examiner*—W. Gary Jones
*Assistant Examiner*—Bardley L. Sisson
*Attorney, Agent, or Firm*—Theodore J. Leitereg; Linda J. Nyari; Shelley G. Precivale

[57] ABSTRACT

A method for carrying out an immunoassay for an analyte in which a sample suspected of containing an analyte and reagents useful for detecting the analyte of interest are combined in an aqueous medium, wherein one of the reagents includes a support and one includes a label, the improvement comprising employing as the reagents a first and second conjugate, each comprised of a specific binding pair (sbp) member bound to a small molecule wherein the small molecules of each conjugate are different.

12 Claims, No Drawings

5,512,659

COMPOSITIONS USEFUL IN HETEROGENEOUS IMMUNOASSAYS

BACKGROUND OF THE INVENTION

Heterogeneous immunoassays require a means be provided to separate a labeled binding reagent from an unlabeled binding reagent. Frequently, a surface is provided to which is bound a specific binding ligand or receptor. Various surfaces have been used, such as latex beads, which can be filtered; tubes or wells, usually plastic, which also serve as the container for the assay mixture; magnetic particles which can be separated in a magnetic field gradient; insoluble polymers which are separated by centrifugation or are used as the stationary phase of a chromatograph; bibulous materials such as cellulose or glass paper through which reagents can be filtered or transferred by capillary action.

U.S. Pat. No. 4,659,678 describes a method for carrying out an immunoassay in which an antibody labeled with a hapten forms a complex with the analyte in a liquid medium, The complex binds to a solid support to which is bound antibodies to the hapten. Detection of the bound sample is measured using a second antibody to the analyte labeled with reagents such as radioactive iodine, a fluorescer or an enzyme.

U.S. Pat. No. 4,298,685 describes an assay method using antigens covalently linked to an enzyme, a biotinylated antibody and an avidin coated surface. A competitive immunoassay system is described which is suitable for diagnostic assays.

European Patent Application 0 201 079 describes a sandwich immunoassay having biotin attached to one antibody, a second antibody attached to a detectable label and a binding substance for biotin attached to a solid support.

U.S. Pat. No. 4,228,237 describes a method for determining the presence of a ligand in a liquid medium which utilizes enzyme labeled avidin and a biotin labeled reagent. The resulting enzyme activity is related to the quantity of ligand present in the sample.

United Kingdom Application 2 084 317 describes a competitive immunoassay for an antigen which utilizes a solid surface coated with antibody to a hapten or avidin, an antigen-hapten or antigen-biotin conjugate, a soluble antibody to the antigen and an enzyme labeled antibody to the antibody.

U.S. Pat. No. 4,780,423 describes a heterogeneous assay using controlled pore glass particles. The controlled pore glass particles are used in a fluorescent immunoassay as the support for the specific binding partner capable of binding to a ligand. As used in the invention, the glass particles bind a complex of interest, the detection of which is achieved by use of a fluorescent probe. Measurement of fluorescence is carried out in the presence of the glass particles.

The use of solid particles, such as magnetic particles or glass beads, to serve as the support for an immunologic assay is known. An example of such assays include the use of magnetic particles as the solid support in a fluorometric immunoassay as described in U.S. Pat. No. 4,777,145. The use of avidin-coated glass beads in immunoaffinity chromatography and a method for preparing such avidin-coated beads is described by Babashak J. V. and T. M. Phillips, *J. of Chromatography* 444:21 (1988).

The present invention provides a means to carry out various heterogeneous immunoassays using the improved method of the invention so as to achieve high capacity, rapid binding and convenient washing of the stationary phase of the heterogeneous immunoassay without centrifugation or conventional filtration.

SUMMARY OF THE INVENTION

A method for separating a surface bound component in an immunoassay from components dissolved or suspended in a liquid medium is provided wherein a solid support provides the surface for binding and the liquid medium is separated from the support by aspiration through a tube inserted into the reaction vessel. The support will have a number of specific binding pair (sbp) members, usually receptors, affixed to its surface which are capable of binding a complementary sbp member, usually a small molecules, which is bound to a reagent capable of binding the analyte. The separation involves the removal of a receptor for a small molecule that is conjugated to a label and is present in the liquid medium from the same receptor conjugate bound to a support.

One embodiment of the invention describes a method for carrying out an immunoassay for an analyte which comprises providing in an assay medium (a) a sample suspected of containing an analyte and reagents useful for detecting the analyte, wherein one of the reagents includes a support and one includes a label, (b) separating the medium and support, and (c) observing the medium or support for the presence or amount of label. The presence or amount of label is related to the presence or amount of analyte in the sample. The improvement of the method comprises employing as two of the reagents a first and second conjugate, each comprised of a specific binding pair (sbp) member that is complementary to another sbp member in the assay medium, and that is bound to a small molecule wherein the small molecules of each conjugate are different.

Another embodiment of the invention describes a method for carrying out an immunoassay for an analyte which comprises providing in combination in an aqueous medium (1) a first small molecule bound to a member of a first specific binding pair (sbp) which sbp consists of a receptor for the analyte and an analog of the analyte; (2) label bound to a first receptor for the first small molecule; (3) sample suspected of containing the analyte; (4) a member of a second sbp complementary to the analyte or to the member of the first sbp and bound to X where X is a second small molecule (Z) or a second receptor (anti-Z) for the second small molecule; and (5) a support bound to Y, where Y is Z or anti-Z, and Y is substantially different than X. The medium and support are then separated and either the medium or the support are observed for the presence or amount of label. The presence or amount of label is related to the presence or amount of analyte in the sample.

Yet another embodiment of the invention describes a method for carrying out an immunoassay which comprises combining in an aqueous medium: (1) a conjugate (C1) of a first small molecule and (i) a first specific binding pair (sbp) member complementary to the analyte (A) or (ii) an analog of the analyte; (2) sample suspected of containing the analyte; (3) a conjugate (C3) of a second small molecule and a second sbp member complementary to the analyte or an analogs of the analyte wherein at least one of C1 and C3 contains an sbp member complementary to the analyte. The aqueous medium is combined, simultaneously with the reagents of (1) through (3) or after incubation following the combination of the reagents, with a support (S) bound to a second receptor for the second small molecule under conditions wherein a complex containing the conjugate (C1) becomes bound to the support as a function of the presence of the analyte in the sample. The medium and the support are incubated and then separated and a solution of a conjugate (C2) of a label and a first receptor for the first small molecule is combined with the support when the conjugate (C2) is not present in the aqueous medium. The support is then observed for the presence or amount of label, usually after separation from the solution of conjugate (C2).

Still another embodiment of the invention describes a method for carrying out an immunoassay for the detection of an analyte in a sample which comprises combining in an aqueous medium: (1) a conjugate (C'1) of a first small molecule and an analog of the analyte; (2) a sample suspected of containing the analyte; (3) a conjugate (C'3) of a second small molecule and an antibody complementary to one of the analyte; and (4) a conjugate (C'2) of a label and an antibody complementary to one of the small molecules. The reagents are combined simultaneously with the aqueous medium and a support (S) bound to a receptor for the other of the small molecules that is not complementary to the antibody of conjugate (C'2) under conditions wherein a complex having the label becomes bound to the surface of the support in inverse relation to the amount of analyte present in the sample. The medium and support are separated and either the medium or the support are observed for the presence or amount of label.

In another embodiment of the invention an assay for detecting a monoepitopic antigen suspected of being present in a sample is described which comprises the step of forming in inverse relation to the amount of antigen in the sample a complex of the form (1) Label-$Ab_F$: F-$Ab_{hapten}$: hapten-X:Y-support; or (2) Label-$Ab_F$:F-hapten:$Ab_{hapten}$-X: Y-support wherein Label-$Ab_F$ is an antibody to a first small molecule (F) bound to a label; F-hapten and hapten-X are small molecules (F or X) bound to an analog of the antigen; $Ab_{hapten}$-X and F-$Ab_{hapten}$ are conjugates of anti-hapten antibody with a second small molecule (X or F); and Y-support is a receptor bound to a support.

In still another embodiment of the invention, a composition of matter consisting of a conjugate of a monoepitopic antigen covalently bound to a small molecule is described in which the conjugate is bound in a termolecular complex with an antibody for the monoepitopic antigen and an antibody for the small molecule.

In another embodiment of the invention, a method for carrying out an assay for the detection of an antibody analyte (A) in a sample is described which comprises combining in an aqueous medium: (1) a conjugate (C"1) of a first small molecule and an antibody complementary to the antibody analyte or an antigen for the antibody analyte; (2) a conjugate (C"2) of a label and a first receptor for the first small molecule; (3) sample suspected of containing the antibody analyte; and (4) a conjugate (C"3) of a second antibody complementary to the antibody analyte or an antigen for the antibody analyte and a second small molecule. The reagents in the aqueous medium are combined simultaneously or after incubation with a support (S) bound to a second receptor for the second small molecule under conditions wherein a complex containing the label becomes bound to the surface of the support as a function of the presence of the analyte in the sample. Following the combination of the reagents the medium is separated from the support and either the medium or the support are observed for the presence or amount of label, the presence or amount of label being related to the presence or amount of antibody in the sample.

In still another embodiment of the invention is described a composition of matter:

E-$Ab_F$:F-hapten:$Ab_{hapten}$-X: Y-support where E-$Ab_F$ is an anti-fluorescein antibody bound to an enzyme; F-hapten is a fluorescein bound hapten; $Ab_{hapten}$-X is an anti-hapten antibody bound to biotin; and Y-support is avidin bound to a support.

In another embodiment of the invention an assay for detecting a hapten present in a sample is described which comprises the step of forming a complex Label-$Ab_F$:F-hapten:$Ab_{hapten}$-X: Y-support where Label-$Ab_F$ is an anti-fluorescein antibody bound to an enzyme; F-hapten is a fluorescein bound hapten; $Ab_{hapten}$-X is an anti-hapten antibody bound to biotin; and Y-support is avidin bound to a support.

In still another embodiment of the invention is described a composition of matter E-$Ab_F$:F-$Ab_1$:Analyte:$Ab_2$-X:Y-support where: E-$Ab_F$ is an anti-fluorescein antibody bound to an enzyme; F-$Ab_1$ is a fluorescein bound first antibody; $Ab_2$-X is a second antibody to the analyte and bound to biotin; and Y-support is avidin bound to a support.

In another embodiment of the invention is described an assay for detecting an analyte present in a sample comprising the step of forming a complex Label-$Ab_F$:F-$Ab_1$:Analyte:$Ab_2$-X:Y-support where Label-$Ab_F$ is an anti-fluorescein antibody bound to an enzyme; F-$Ab_1$ is a fluorescein bound first antibody to the analyte; $Ab_2$-X is a second antibody to the analyte and bound to biotin; and Y-support is avidin bound to a support.

In still another embodiment of the invention, is described a composition of matter of the form (1) E-$Ab_F$:F-Ab:Ab:Ag-X:Y-support; or (2) E-$Ab_F$:F-Ag:Ab:Ab-X:Y-support where E-$Ab_F$ is an antibody to a first small molecule bound to an enzyme; F-Ag and F-Ab are a first small molecule (F) bound to antibody to an immunoglobulin and complementary to the antibody present in a sample, respectively; Ab is antibody present in the sample; Ab-X and Ag-X are a second small molecule (X) bound to antigen complementary to antibody in the sample and bound to biotin; and Y-support is avidin bound to a support.

In still another embodiment of the invention a composition of matter

E-$Ab_F$:F-$Ab_1$:A:$Ab_2$-X is described where E-$Ab_F$ is an anti-F antibody bound to an enzyme, where F is a first small molecule; F-$Ab_1$ is said first small molecule (F) bound to a first antibody; A is a multiepitopic antigen; and $Ab_2$-X is a second antibody bound to a second small molecule.

In another embodiment of the invention a kit for carrying out an immunoassay for an analyte is described which comprises in packaged form (a) a conjugate of a first small molecule and a first sbp member complementary said analyte, (b) a conjugate of a second small molecule and a second sbp member that is an analog of or complementary to said analyte, (c) a conjugate of a receptor for one of said small molecules and an enzyme, (d) a substrate for said enzyme, and (e) a support comprised of a surface bound to a receptor for the other small molecule.

DETAILED DESCRIPTION OF THE INVENTION

This invention provides an immunoassay method which is more versatile and convenient than the known immunoassays. The invention has particular application to the assay of an analyte in a sample where a separation step is required.

Before proceeding further with the description of the specific embodiments of the present invention, a number of terms will be defined.

"Analyte" means the compound or composition to be measured in a sample that is the material of interest. The analyte is a member of a specific binding pair (sbp) and may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a blood group antigen (A, B, AB, O, D, etc.) or an HLA antigen. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, androgens, androcortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, ntihistamines, anticholinergic drugs, such as attopine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$ more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member") means one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, IgG-protein A, and the like are not immunological pairs but are included in the invention.

"Ligand" means any organic compound for which a receptor naturally exists or can be prepared.

"Receptor" means any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, protein A, complement component Clq, and the like.

"Hapten" means a ligand of molecular weight 100 to 1,000,000 or more but usually if molecular weight of 100–2000, which can bind to a complementary sbp member, either an antibody or other receptor, wherein the ligand is an analog of an analyte differing from the analyte by at least the presence a bond to a small molecule and can compete with the analyte for binding to the sbp member. Examples of haptens include derivatives of vitamins B12, folic acid, digoxin, thyroxine, etc. Examples of sbp members corresponding to these haptens are intrinsic factor, folate binding protein, anti-digoxin antibody and antithyroxine antibody, respectively. The term hapten is also intended to apply to high molecular weight ligands such as thyroid binding globulin, albumin, immunoglobulins, etc., particularly when the corresponding analyte is expected to be present in relatively high concentration in the samples, provided that the ligand can compete with the analyte for binding to the sbp member.

"Support" means any non-porous or porous surface. Typical support surfaces include glass or plastic beads, latex or cellulose particles, glass or cellulose filter paper, nitrocellulose membranes, polystyrene plates, magnetic particles, plastic tubes or vessels, and the like. The support may be of any convenient material to which a sbp member can be non-diffusively bound and which does not dissolve in or react adversely with the ligand medium. Usually the support will be plastic such as polystyrene, polycarbonate, polyacrylate, polyvinylchloride, polyurethane, teflon and the like or it may be metallic such as steel, nickel, copper, gold and preferably will be ceramic including, for example, quartz, glass, and the like. When the support is a matrix of beads, the beads will usually be of a defined approximately uniform, size, preferably 0.2 to 2.5 mm, and will have either a rough or smooth surface, preferably smooth. Preferably the beads are rounded or oblong, usually approximately spherical and have surface properties which minimize non-specific binding. As used in the immunoassays of the invention, the support will have bound to it, an sbp member, which may be a ligand such as biotin or a receptor, preferably a receptor such as an antibody, avidin, apoenzyme, repressor protein, intrinsic factor and the like.

"Small molecule" means an organic or organometallic group, having a molecular weight of from 100 to 2000, preferably 150 to 1000, usually bonded to an sbp member or a support and for which a receptor exists or can be prepared. Examples of small molecules useful in the invention include derivatives of biotin, lysergic acid, brucine, fluorescein, vitamin B12 and in general molecules that are not usually found in high concentration in the samples to be assayed. For biological samples, highly toxic molecules and synthetically derived molecules other than drugs are often preferred.

"Conjugate" means a specific binding pair member such as a ligand or receptor, usually an antibody bound covalently or non-covalently, usually covalently to one or many small molecules or labels. The conjugate may be one or more small molecules bound to a hapten or to a receptor complementary to an analyte.

"Label" means a member of the signal producing system that is covalently bound to a receptor complementary to a small molecule. The label can be isotopic or non-isotopic, usually non-isotopic, including catalysts such as an enzyme, a chromogen such as a fluorescer, dye or chemiluminescer, a metallic particle, and so forth.

"Signal producing system" means a signal producing system having one or more components, at least one component being a label. The signal producing system generates a signal that relates to the presence or amount of analyte in a sample. The signal producing system includes all of the reagents required to produce a measurable signal. The label will usually be conjugated directly or indirectly to a receptor for a small molecule. Components of the signal producing system may be chemiluminescers, radioactive substances, coenzymes, substances that react with enzymic products, enzymes, and catalysts, solid particles, fluorophors, chromophors, gold particles and the like. The signal producing system provides a signal detectable by external means, preferably by measurement of the degree of aggregation of particles or by use of electromagnetic radiation, desirably by visual examination. For the most part, the signal producing system will involve, a chromophoric substrate and enzyme, where chromophoric substrates are enzymatically converted to dyes which absorb light in the ultraviolet or visible region, phosphors, fluorescers or chemiluminescers, radioactive atoms, electroactive groups, and the like.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

Of particular interest are enzymes which involve the production of hydrogen peroxide and the use of the hydrogen peroxide to oxidize a dye precursor to a dye. Particular combinations include saccharide oxidases, e.g., glucose and galactose oxidass, or heterocyclic oxidases, such as uricase and xanthine oxidass, coupled with an enzyme which employs the hydrogen peroxide to oxidize a dye precursor, that is, a peroxidase such as horseradish peroxidase, lactoperoxidase, or microperoxidase. Other enzymes which are of particular interest in the subject invention include β-galactosidase, urease, and alkaline phosphatase.

"Non-specific binding" means non-covalent binding of a label or molecule to a surface that is relatively independent of the specific structure of the molecule that becomes bound. Such non-specific binding can result from charge or electrostatic interactions, hydrophobic interactions, hydrogen bonding, Van der Waals forces, and the like.

"Ancillary materials" means various additional materials employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

As mentioned above, one aspect of the present invention involves a method for separating a receptor-label conjugate bound to a support from the same conjugate in solution in a liquid medium. The method comprises combining a liquid medium containing the conjugate with a support to which is bound an sbp member capable of direct or indirect binding to the conjugate in relation to the amount of analyte present in the solution. In a preferred practice of the invention, the solid support is a matrix of beads. In order to achieve complete separation, the liquid medium containing the conjugate is of a volume that is not significantly in excess of that needed to completely cover the matrix of beads and may be insufficient to cover the beads and the amount of sbp member bound to the beads will be at least sufficient to bind all the conjugate. Included within the invention, however, is a separation method wherein the volume of liquid is substantially greater than the volume required to cover the beads. In either instance, the method for conducting the separation remains the same. After incubation the liquid medium is first incubated with the matrix, which will usually be carried out in a vessel that is not otherwise equipped with a filtration device and is therefore impermeable to the liquid. The medium is then separated from the beads by means of aspiration. The aspiration is carried out using an aspiration tube having one or more orifices, preferably one orifice having, when the tube has a circular cross section, a diameter smaller than the diameter of the smallest bead with which it comes in contact. When the tube cross section is not circular at least the shortest or the longest cross sectional diameter of the orifice must be smaller than the corresponding bead diameter. As a result the liquid is efficiently separated from the matrix without loss of beads.

The reagents used in immunoassay of this invention are of particular importance in the design of this invention. As designed, the methodology consists of certain reagents which are generic to most analytes, thereby providing for easier automation and control of stability of reagents in an immunoassay systems.

In one practice of the invention, a methodology for the detection of a monoepitopic antigen, such as a drug, in a sample is set forth. The methodology employs a competitive assay arrangement such that a conjugate of a hapten bound to a first small molecule will compete with antigen in the sample for binding to a conjugate of anti-hapten antibody bound to a second small molecule. The amount of a complex of hapten conjugate and anti-hapten conjugate that forms will be related to the amount of analyte. The resulting complex binds to the solid support to which a receptor to one of the small molecules is bound. Before or after binding to the support, a conjugate of a receptor to the other small molecule and a label is combined with the complex. Schematic representations of the complexes formed by this methodology of the invention as applied to detection of haptens is as follows:

$$\text{E-Ab}_F: \text{F-hapten: Ab}_{hapten}\text{-X: Y-support}$$

$$\text{E-Ab}_F: \text{F-Ab}_{hapten}: \text{hapten-X: Y-support}$$

where $\text{E-Ab}_F$ is a receptor for a small molecule (F) bound to a label, for example anti-fluorescein antibody bound to an enzyme; F-hapten and hapten-X are small molecules (F or X) such as fluorescein or biotin bound to a hapten; $\text{Ab}_{hapten}\text{-X}$ and $\text{F-Ab}_{hapten}$ are conjugates of anti-hapten antibody with a second small molecule (X or F) such as biotin or fluorescein; and Y-support is a receptor, such as avidin, for X bound to a support.

In another application of the invention, the assay methodology is designed to be particularly suited for assaying of analytes in a sample having at least two determinants, that is, at least two sites to which receptors can simultaneously bind. In a preferred practice of the invention, the methodology of this assay utilizes the following reagents: a label bound to a receptor for a small molecule, for example an enzyme bound to anti-fluorescein; a first antibody complementary to a first determinant site on the analyte and to which is bound a small molecule, such as fluorescein; a second antibody complementary to a second determinant on the analyte and to which is bound a second small molecule, such as biotin; a sample suspected of containing the analyte of interest; and a support to which is bound a receptor for the second small molecule, as for example, avidin. The antibodies of the assay can be monoclonal or polyclonal, preferably monoclonal. In such an assay system, the amount of label that will become bound to the solid support will be directly related to the amount of analyte present in the sample. In particular, the receptor for the first small molecule to which is bound a label will bind to the first small molecule bound to the first antibody. In the presence of analyte, the first antibody will bind to the analyte at the first determinant site. The second antibody to which is bound the second small molecule will bind to the analyte at the second determinant site. In turn, the second small molecule on the second antibody binds to the receptor for the second small molecule bound to the support which results in the complex of interest binding to the support. The reagents and sample can be combined simultaneously or wholly or partially sequentially with each other and with the solid support and will preferably be combined prior to introduction to the solid support except that the label bound to a receptor may alternatively be added to the support after the support has been in contact with all the other reagents. A schematic representation of the complex formed in the immunoassay of the invention as applied to detection of analytes is as follows:

$$\text{E-Ab}_F: \text{F-Ab}_1: \text{A: Ab}_2\text{-X: Y-support}$$

where $\text{E-Ab}_F$ is a receptor for a first small molecule, such as anti-fluorescein antibody, bound to a label, such as an enzyme; $\text{F-Ab}_1$ is a first small molecule, such as fluorescein, bound to a first antibody for the analyte; A is an analyte of interest present in a sample; $\text{Ab}_2\text{-X}$ is a second small molecule such as biotin bound to a second antibody for the analyte; and Y-support is a receptor, such as avidin for the second small molecule bound to a support.

The assay methodology of the invention is especially suited for the detection of microbiological antigens, in particular, antigens produced in infectious diseases, for example, chlamydia, the human immunodeficiency virus (HIV-1) associated with AIDS, and the like.

The assay methodology of the invention is also suitable for the detection of antibodies. In a preferred practice of the invention such an immunoassay system utilizes the following reagents: enzyme bound to anti-fluorescein antibody; an analog of the antigen which is complementary to the antibody analyte which is bound to fluorescein; sample suspected of containing the antibody; an antibody to an immunoglobulin bound to biotin; and an avidin bound support. Using this immunoassay methodology, if the sample of interest contains the antibody, a complex containing the enzyme will be bound to the support. The presence of enzymatic activity on the support after separation of unbound enzyme correlates with the presence of the antibody in the sample. One variation of such an assay would include, for example, the replacement of the fluorescein bound antigen with an antibody to an immunoglobulin bound to fluorescein and replacement of the antibody to an immunoglobulin bound to biotin with antigen bound to biotin. Schematic representations of the complexes formed in the methodology of the invention as applied to detection of specific antibodies present in a sample are as follows:

$$\text{E-Ab}_F: \text{F-Ag: Ab: Ab-X: Y-support}$$

$$\text{E-Ab}_F: \text{F-Ab: Ab: Ag-X: Y-support}$$

where $\text{E-Ab}_F$ is an antibody to a first small molecule bound to a label; F-Ab and F-Ag are the first small molecule (F)

bound to antibody to an immunoglobulin and bound to antigen complementary to antibody present in the sample, respectively; Ab is the antibody of interest present in the sample; and Ag-X and Ab-X are a second molecule (X) bound to antigen complementary to antibody in the sample and bound to an antibody complementary to antibody in the sample.

In yet another application of the invention, the immunoassay methodology is designed to detect the presence of IgM in a sample. In particular, the assay methodology is particularly suited to the detection of the antibody to the hepatitis core antigen. In such an assay system, the following components may be utilized: enzyme bound to anti-fluorescein antibody; antigen bound to fluorescein; sample; anti-human IgM bound to biotin; and an avidin coated support. If the IgM is present in the sample, a complex is formed which can be detected. The degree of enzymatic activity correlates to the concentration of IgM in the sample. In a variation on such an assay, the fluorescein is bound to an anti-antigen antibody rather than directly to the antigen.

The design of the assay system makes it possible to use reagents which are generic, i.e. can be used in any assay system no matter what the analyte of interest. As is apparent in the above examples, each assay uses the conjugates comprising a receptor bound to a small molecule.

In each of the foregoing methodologies a conjugate (C1) of a first small molecule and a first sbp member non-covalently binds directly to a conjugate (C2) of a receptor for the first small molecule and a label, and also non-covalently binds to a conjugate (C3) of a second small molecule and a second sbp member, wherein the binding between C1 and C3 is direct when the assay is for an analyte with only one determinant site and is otherwise direct or indirect, usually indirect, when the assay is for an analyte with multiple determinant sites. Conjugate C3 further non-covalently binds directly to a support (S) comprising a receptor for the second small molecule bound to a surface. When all of the binding events required in the assay have been completed a complex of the following composition is formed:

C2:C1:(A)n:C3:S in which A is a molecule of the analyte and n is 0 when only one sbp member is available to bind to A, such as when the analyte has a single determinant site, and n is 1 when the analyte has multiple determinant sites.

In carrying out the assay there are certain sequences of steps that are more convenient and others that provide the highest assay sensitivity. The choice of the particular sequence to be employed will therefore depend upon the needs of the person performing the assay. In general it will be preferable to first combine the sample, C1, C2, and C3 in an aqueous medium, usually without regard to the order of addition, except that for competitive assays for analytes with a single determinant site it will usually be preferable to combine the conjugate containing an sbp member complementary to the analyte with the sample at the same time or prior to combining it with the conjugate containing an analog of the analyte. The aqueous medium containing the sample, C1, C2, and C3, is then optionally incubated for a period of up to an hour or more and then combined with the support (S) and usually further incubated for a period of 5 seconds to 5 hours, usually one minute to one hour. The amount of label bound to the support or remaining in the medium may then be measured directly but will usually be measured following separation of the medium from the support.

Another protocol that may be used that provides added convenience but may increase the incubation time required to achieve a particular assay sensitivity is to combine essentially simultaneously the sample and all of the reagents C1, C2, C3 and S followed by incubation for up to 5 hours and then detection of the label on the support (S) or in the medium before or after, usually after, separation of the medium and the support.

Another protocol that may be used that provides increased sensitivity is to sequentially add solutions of C3, sample, C1 and C2 to the support with or without incubation following each addition and with or without separation of each solution from the support prior to adding the next solution. Following addition of the solution of C2 to the support the label will be detected on the support or in the aqueous medium before or after, usually after, separation of the medium and the support.

In a particularly preferred protocol the sample is combined in an aqueous medium with C1 and C3 prior to or simultaneous with combination of the medium with the support. After optionally incubating the medium with the support, the support is separated from the medium and combined with a solution containing C2. Following incubation of C2 with the support, the label is detected on the support or in the aqueous medium before or after, usually after, separation of the solution and the support.

In these assays any convenient label can be used. These may include enzymes as, for example, phosphatases such as alkaline phosphatase, peroxidases such as horseradish peroxidase (HRP), urease, glycosidases such as β-galactosidase, oxidases such as glucose oxidase, esterases such as choline esterase, nucleotide polymerase such as Q-beta-replicase, penicillinase, luciferases and the like. Alternatively, enzyme inhibitors such as an antibody to an enzyme or a mechanism-based inhibitor, or enzyme activators such as an enzyme prosthetic group, or derivatives of coenzymes such as NAD, NADH, NADP, ATP, FAD, FMN, can be used. Alternatively, fluorophores such as derivatives of fluorescein, umbelliferone, oxazines, acridinium salts, acridones, pyrenes, squatate dyes, fluorescent rare earth chelates, cyanines, merocyanines, phycobiliproteins, bimanes, naphthylamines, and the like can be used. Another useful type of label is a chemiluminescent label including derivatives of dioxtanes, luminol, firefly luciferin, acridinum esters. Particulate labels can also be used, preferably if they are less than 100 nm in diameter and particularly preferable if they carry a detectible molecule or are themselves readily detectible. Useful particulate labels include colloidal gold, colloidal selenium, dyed latex beads, liposomes bound to or occluding a detectible molecule, dye particles or crystallites, etc. Additional labels include radioactive atoms; electroactive labels such as organomercury compounds, hydroquinones, benzidines, ferrocenes, alpha-diketones, hydroxylamines, and hydrazines; and catalysts other than enzymes such as phenazine methosulfate, and Meldola blue.

The labels will normally be bonded covalently to a receptor for a small molecule, usually an antibody. Bonding may be by simply replacing a hydrogen atom of the label with a bond to the receptor or may include a linking group between the label and the receptor of any size but preferably no larger than necessary to permit unfettered binding of an sbp member complementary to the sbp member bound to the label and to permit signal production by the label. Generally the linking group will be a bond or a group of from 1 to 100 atoms, usually from 1 to 15 atoms.

The conjugates of this invention containing a small molecule bound to an sbp member will contain small molecules for which a natural receptor exists or can be prepared. The small molecules will usually be neither extremely hydrophilic nor extremely hydrophobic and will preferably be structurally dissimilar to substances that are likely to be present in the sample. When the conjugate consists of a small molecule bonded to a hapten the small molecule will be attached to the hapten through a chain of atoms that will preferably be at least 10 atoms long, frequently at least 20 atoms long, but may be shorter or longer, the critical consideration being that the chain must be long enough to allow simultaneous binding to the conjugate by a receptor for the small molecule and by an sbp member complementary with the sbp member in the conjugate. The hapten conjugates will usually have one hapten bound to one small molecule but included in the scope of the invention are hapten conjugates that have more than one small molecule bonded to a hapten. Conjugates of small molecules with sbp members that have multiple determinant sites or are receptors will have at least one and frequently 2–20 small molecules in the conjugate which will usually be bound covalently. Bonding may be by simply replacing a hydrogen atom of the small molecule with a bond to the sbp member or may include a linking group between the small molecule and the sbp member of any size but preferably no larger than necessary to permit binding to the conjugate of both a receptor for the small molecule and an sbp member complementary to the sbp member in the conjugate.

The support in this invention will normally be particulate such as beads, liposomes, cells, sols, and the like; bibulous materials such as porous membranes, cellulosic paper, glass paper, and nitrocellulose membranes; or non-porous materials such as glass, plastic, metal, ceramic, and the like. A receptor will be covalently or non-covalently bonded to the surface of the support in such a manner as to permit ready binding of a conjugate containing a small molecule ligand complementary to the receptor. Normally bonding of the receptor to the surface will be achieved by incubating the surface with the receptor, wherein the surface may previously have been treated with a reagent to enhance binding such as polycations, for example polylysine; carbodimiides; silylating agents; bifunctional cross linking reagents such as carbonyl diimidazole; periodate; and similar activating reagents. Alternatively the support may be prepared with an sbp member complementary to the receptor such as the ligand for the receptor or an antibody against the receptor already bound to the surface. Incubation of the receptor with such a surface will then cause the receptor to bind non-covalently. When this method of binding is employed wherein a ligand for the receptor is initially present on the surface, the receptor will normally have at least two binding sites for the ligand.

In carrying out the invention, a liquid, usually aqueous, medium will be employed. Other polar solvents may also be employed, usually oxygenated organic solvents from one to six, more usually from one to four, carbon atoms, including alcohols, ethers, and the like. Usually these cosolvents will be present in less than about 40 weight percent, more usually in less than about 20 weight percent. Generally, a pH range of 5 to 10, more usually 6 to 9, will be used. Another consideration with respect to the pH of the assay is the maintenance of a significant level of binding of sbp members while optimizing signal producing proficiency. In some instances, a compromise will be made between these considerations. Various buffers may be used to achieve the desired pH and maintain the pH during the determination. Illustrative buffers include borate, phosphate, carbonate, Tris, barbital, and the like. The particular buffer employed is not critical to this invention; however, in individual separations or individual assays, one buffer may be preferred over another.

Moderate temperatures are normally employed for carrying out the separation and assay and usually constant temperatures during the period for conducting the assay. The temperature for the assay, particularly involving an immunoassay, will generally range from about 0° to 50° C., more usually from about 15° to 40° C.

While the concentrations of the various reagents will generally be determined by the concentration range of the sbp member in the liquid medium or of the analyte in an assay, the final concentration of each of the reagents will normally be determined empirically to optimize the sensitivity and specificity of the separation or of the assay over the range of interest.

In the immunoassay of the invention, the aqueous medium can also contain one or more members of a signal producing system. The concentration of the various members of the signal producing system will vary and be dependent upon the concentration range of interest of the analyte and the type of measurement or assay involved. As a general point, the concentration of the various members of the signal producing system will be selected to optimize the sensitivity of the assay within the concentration range of interest of the analyte.

As a matter of convenience, the reagents for conducting an assay can be provided in a kit in package combination in predetermined amounts for use in assaying for an analyte. The kit comprises (a) a conjugate of a first small molecule and a first sbp member complementary to the analyte, and (b) a conjugate of a second small molecule and a second sbp member that is an analog of or complementary to the analyte. The kit may also include a conjugate of a label and a receptor for one of the small molecules and a support comprised of a surface bound to a receptor for the other small molecule. The kit can also include other reagents for generating a signal in relation to the amount of analyte in the sample. Ancillary agents can be included as necessary.

Preferably reagents for determining the presence or amount of an analyte in a sample can be packaged in a kit comprised of (a) a conjugate of a first small molecule and a first sbp member complementary to the analyte, (b) a conjugate of a second small molecule and a second sbp member that is an analog of or complementary to the analyte, (c) a conjugate of receptor for one of the small molecules and an enzyme, (d) a substrate for the enzyme, and optionally (e) other members of a signal producing system, a support comprised of a surface bound to a receptor for the other small molecule, and ancillary reagents.

In the invention described herein, when the solid support is a matrix of beads, the beads are usually non-porous, usually glass or latex and normally are between 0.2 and 2.5 mm average diameter. Most preferably, the beads are from 0.5 to 2 mm average diameter. The beads are usually approximately spherical and may have a rough or smooth surface.

To be of value in the immunoassay, the beads must have specific surface properties. The surface must have low non-specific binding to the label and spb members while providing an efficient means of separation of label that is bound to analyte or its complementary sbp member from label that is unbound. The size and shape of the beads is selected to maximize the ratio of bead surface to the volume of the liquid medium while permitting easy penetration of the aspiration tube into the bead matrix and efficient separation of the liquid medium from the matrix. A higher surface to volume ratio permits more rapid binding of the label to the beads but necessitates use of smaller beads that can interfere with efficient separation. Normally beads ranging in size from 0.2 to 2.5 mm have been found to be most useful. In addition it will frequently be desirable to maximize the surface density of sbp members on the beads in order to maximize their binding capacity. In general surface densities should be least one sbp member molecule per 10,000 $nm^2$, preferably at least one per 1000 $nm^2$, most preferable at least one per 100 $nm^2$ and will preferably be sufficiently high to bind all of the complementary sbp member present in the assay medium that contacts the beads.

Because of the high surface area of beads, attention must be paid to the surface properties so that background non-specific binding remains low. Where avidin is used as the receptor bound to the beads, non-specific binding can be reduced by drying the glass particles in the presence of sucrose after the binding of avidin to the beads. Examples of coatings in addition to sugars, which have been found useful include bovine serum albumin (BSA), poly(vinylalcohol), casein and non-fat milk.

Whatever type of solid support is used it must be treated so as to have a receptor bound to its surface which receptor will specifically bind to a small molecule. In a preferred practice of the invention, the support will have bound to it a ligand or receptor that will permit the support to be used for a variety of different assays. For example, avidin can be covalently bound to spherical glass beads of 0.5 to 1.5 mm. A matrix of these beads is mixed in an aqueous medium with biotin-labeled antibodies to an analyte, a sample containing the analyte, and a labeled antibody or ligand that will bind to the biotin-labeled antibodies as a function of the amount of analyte in the solution. Because the beads bind to biotin and biotin can be bound to any antibody, the same beads can be used for most antibody-antigen pairs. After sufficient incubation to permit binding of the labeled antibody or ligand to the biotinylated antibody and binding of the latter to the beads, the solution is removed from the beads by aspiration. Wash solution is then added by means of the same or a different tube and liquid again aspirated. After repeating the washing cycle, the label is detected and the amount of label is related to the amount of analyte in the sample.

Use of the method of the invention is applicable to any heterogeneous binding assay for an analyte. Specific assays include for example, assays for digoxin, triidothyronine (T3), thyroid stimulating hormone (TSH), thyroid binding globulin (TBG), vitamin B12, hepatitis antigens (e.g. $HB_sAg$) and hepatitis antibodies, the human immunodeficiency virus (HIV) related antigens and antibodies. In each system, biotinylated antibody or biotinylated antigen that is complementary to the analyte is used. Receptors other than avidin (which includes strepavidin) may be attached to the beads, such as antibodies, protein A, intrinsic factor, Protein G, Clq, lectins, apoenzymes and the like, whereupon the complementary small molecules conjugated to a sbp member complementary or analogous to the analyte is used.

In a preferred embodiment of the invention all assays use the same two generic reagents, non-porous beads bound to a generic receptor such as avidin and an enzyme bound to a second generic receptor such as anti-fluorescein. In each of these assays two additional sbp members are used, one conjugated to biotin and one conjugated to fluorescein. In such an assay the biotin and fluorescein bound sbp members are allowed to bind with each other or with the analyte in the solution phase prior to combining with the bead matrix wherein the binding reaction proceeds more rapidly then when binding of analyte occurs at a surface as normally occurs in an enzyme linked immunosorbent assay (ELISA).

In an assay for a multiepitopic analyte such as TSH specific TSH, antibodies are conjugated to biotin for later capture by avidin coated glass beads The second TSH specific antibody is conjugated to fluorescein. The enzyme conjugate has at least one HRP linked to an anti-fluorescein antibody. After a short incubation of a mixture of all of the components, glass beads coated with avidin are added to bind the complex (biotin-antibody:TSH:antibody-fluorescein:anti-fluorescein-HRP) to the surface.

A matrix containing a sufficient amount of beads is added such that the entire antibody-sample incubation volume is completely entrapped within the spaces between the beads. This maximizes the surface to volume ratio and provides for relatively short diffusion distances and thereby permits quantitative binding of the biotinylated antibody without shaking.

The surface of the beads is then washed by plunging an aspiration tube to the bottom of the matrix of beads and successively adding and aspirating wash solution. Due to the density and size of the beads, the beads can be easily suspended by the jet of wash solution and then settle quickly. The beads are large enough that they are not aspirated by the wash probe. Substrate is then added and the amount of enzyme product is determined photometrically after a suitable incubation time and compared to the amount of product provided using a sample of known concentration of analyte.

The chemistry and methodology of the invention in certain preferred embodiments have the following significant advantages over the standard ELISA chemistry: 1) receptor bound supports are generic to all assays; 2) analyte to antibody binding in solution phase results in very rapid kinetics compared to those achieved with antibody immobilized on a solid surface; 3) presence of a large surface area with high antibody binding capacity results in rapid kinetics of capture; and 4) the capture surface need not be added quantitatively. In addition, the receptor-label conjugate is generic to all assays and will be the only label reagent to optimize and stabilize. This is in contrast to the standard heterogeneous immunoassay formats where separate labeled reagents are required for each assay. The chemistry to link small molecules such as biotin or fluorescein to antibodies or haptens is simple and efficient. (See, for example, D. M. Boorsma, *Immunocytochemistry* 2:155 (1983)). The stability of the small molecule conjugates will be as good as the antibodies used in the conjugate.

EXAMPLES

The examples which follow are illustrative and not limiting of the invention. Unless otherwise indicated, reagents were obtained from commercial sources and, where applicable, were used according to manufacturer's directions.

The following abbreviations are used throughout the examples:

| | |
|---|---|
| $Ab_{Dig}$ | antidigoxin antibody |
| $Ab_F$ | anti-fluorescein antibody |
| $Ab_{T3}$ | anti-triiodothyronine antibody |
| ANS | 8-Anilinonaphthalene-1-sulfonic acid |
| Biotin-LC-NHS | succinimidyl 6-(biotinamido) hexanoate |
| Bis-$NH_2$ | 2,2'-Oxybis(ethylamine) |
| BSA | Bovine serum albumin |
| DCC | N,N'-Dicyclohexylcarbodiimide |
| Dig | Digoxin |
| Dig-CMO | Digoxin carboxymethyl oxime |
| Dig-LC-F | digoxin carboxymethyl oxime-LC-NH- |

-continued

| | |
|---|---|
| | carboxyfluorescein |
| F | Fluorescein |
| EDAC | 1-ethyl3(3-Dimethylaminopropyl)carboiimide |
| EDTA | ethylenediaminetetraacetic acid, tetrasodium salt |
| F | Fluorescein |
| F-COOH | 6-Carboxyfluorescein |
| F-LC-NH$_2$ | carboxyfluorescein-LC-NH$_2$ |
| GB | Glass beads |
| HRP | Horseradish peroxidase |
| LC | 3,3'-diamino-N-methyldipropylamine |
| NaPi | Sodium phosphate buffer |
| NHS | N-Hydroxysuccinimide |
| o/n | overnight |
| PBS | Phosphate-buffered saline |
| Sulfo-NHS | Sulfo-N-hydroxysuccinimide |
| T$_3$ | 3,3',5-triiodo-L-thyronine |
| TMB | 3,3',5,5'-tetramethylbenzidine-2 HCl |
| TNBSA | 2,4,6-Trinitrobenzesulfonic acid |

EXAMPLE 1

Heterogeneous enzyme-based immunoassay for detection of digoxin
Preparation Of Materials
A. Preparation of HRP-succinyl-oxybis (ethylamide)-digoxin 1. Preparation of HRP-succinyl-bis-NH$_2$. The reagent was prepared in two successive steps: 1.) the two reactive amino groups of the native HRP were converted into carboxyl groups by succinylation to HRP-COOH; 2.) the HRP-COOH was then reacted with an excess amount of oxybis(ethylamine) and EDAC to generate HRP-succinyl-bis-NH$_2$.

Succinylation of HRP. Into 2 mL solution of 20mg/mL HRP in 0.1 M Borax at room temperature, 40 µL of 2.5 M succinic anhydride in DMF was added. After stirring for 20', another 40 µL of succinic anhydride solution was added and the mixture incubated for one more hour at room temperature. The small molecular weight materials were removed by purifying the reaction mixture on a Sephadex G-25 column, equilibrated in 0.005 M sodium phosphate buffer (NaPi)/pH=7.0. The HRP-COOH was concentrated to 20 mg/mL HRP-COOH using Amicon YM-10 membrane. The reaction was followed by gel electrophoresis and TNBSA titration of reactive amino groups.

Introduction of reactive amino groups into the succinylated HRP.

To 1 mL of 20 mg/mL of HRP-COOH in 0.005 M NaPi/pH= 7.0, 8.86 mg of solid 2,2'-oxybis(ethylamine) dihydrochloride was added. The pH of the reaction mixture was readjusted to 7.0 using 0.2 M Na$_2$HPO$_4$. Into this mixture 14 mg EDAC was added and the reaction mixture incubated at 4° C. for 2 hours with gentle stirring. The unreacted small molecular weight materials were removed from the HRP-succinyl-bis-NH$_2$ by a Sephadex G-25 column, equilibrated in 0.05 M NaPi, 0.05 M NaCl/pH=7.8. The number of reactive amino groups was determined by TNBSA to be 1.51 per HRP-succinyl-bis-NH$_2$. The HRP-succinyl-bis-NH$_2$ was purified on CM-Sephadex (C-50) and two main products were separated: (1) HRP-succinyl-bis-NH$_2$ with one amino group and (2) HRP-succinyl-bis-NH$_2$ with two amino groups per HRP.

2. Preparation of Digoxin-NHS. A solution, containing 20 mg of Dig-CMO, 5 mg of NHS, and 9 mg of EDAC in 0.2 mL of DMF, was incubated at room temperature by stirring overnight (o/n). After removing the unsoluble materials by filtration, the solvent (DMF) was removed by rotary evaporation. The product was stored desiccated at 4° C.

3. HRP-Succinyl-Oxybis(ethylamide)-Digoxin. To 4 mL of 1.3 mg/mL HRP-succinyl-bis-NH$_2$ (with two reactive amino groups per HRP) in 0.05 M NaPi, 0.05 NaCl/pH=7.8 at 4° C., 1.3 mL of 1 µmole/mL Dig-NHS in DMF was added (4× 324 µL; 325 µL of Dig-NHS solution was added after each 15 minutes). The reaction mixture was then incubated for three hours by stirring at 4° C. The reaction was stopped by adding 150 µL of 2 M glycine/pH= 8.0 and incubating for an additional one hour at room temperature. Finally, the reaction mixture was centrifuged to remove the unsoluble substances and purified on Sephadex G-25 in 0.05 M Borax. The hapten number was estimated to be about 2 by titrating the remaining reactive amino groups using TNBSA. The conjugate was stored at 4° C.

B. Preparation of Ab$_{Dig}$-Biotin

Anti-digoxin antibodies were purified by immobilized Protein A to obtain the Ab IgG fraction. Then the Ab$_{Dig}$-biotin was prepared by mixing the Ab (about 2–2.5 mg/mL in 0.05 M NaPi, 0.05 M NaCl/pH 7.8) and Biotin-LC-NHS (first solubilized in DMF and a small aliquot used for the reaction) and incubating for three hours at 4° C. In the reaction mixture, the molar ratio of the reactants was Ab:Biotin-LC-NHS=1:25. The uncoupled biotin was removed by Sephadex G-25 column. The final conjugate was stored in 0.05 M NaPi, 0.001% Thimerosal/pH=7.4 at 4° C. or frozen.

C. Preparation Of Dig-LC-F

This reagent was prepared in three successive steps by preparing (1) F-NHS, (2) F-LC-NH$_2$, and (3) Dig-LC-F.

1. Preparation Of F-NHS. To the 2 mL of 100 mg/mL 6-carboxyfluorescein and 30.6 mg/mL of NHS in DMF was added, 0.4 mL of 275 mg/mL of DCC. The mixture was stirred o/n at room temperature in the dark. The formed dicyclohexylurea was removed by filtration. The formation of F-NHS was checked by thin layer chromatography TLC on silica plates, using CH$_2$CH$_2$:methanol:acetic acid=85:15:1 solvent system. DMF was removed by rotary evaporation, and the product (F-NHS) was dried further under strong reduced pressure and stored desiccated at 4° C.

2. Preparation of F-LC-NH$_2$. To the 1.5 mL of LC, 1.2 mL of 125 mg/mL F-NHS in DMF was added and incubated at room temperature o/n, by stirring in the dark. The molar ratio of F-NHS :LC=1:40. The reaction mixture was diluted 1/20 with 0.5 M NaPi/pH 5.0, the pH of the mixture was adjusted to 5.0 by phosphoric acid. The whole mixture was loaded onto a (2.5×10 cm) of BioRex-70 column, equilibrated in 0.5 M NaPi/pH= 5.0. After loading, the column was washed with the starting buffer until all of the 3,3'-diamino-N-methyldipropylamine was removed (monitored with TNBSA reaction). The column was washed with 0.001 M NaPi/pH=6.0 to remove the 6-carboxyfluorescein contaminant. Washing with low ionic strength buffer removes not only the 6-carboxyfluorescein but also fluorescein containing contaminants. The column was washed with dionized water (D-H$_2$O) to remove the salts. Finally, the column was stripped by 0.8 M NH$_4$OH. The ammonium hydroxide was removed by lyophilization. After checking the purity, the product was stored desiccated at −20° C. The reaction was followed (and the purity of the product was checked) by paper electrophoresis (0.05 M NaPi/pH=5.8, 20 minutes and by TLC (C$_{18}$ plates, using 50% methanol in D-H$_2$O as solvent).

3. Preparation of Dig-LC-F. A solution, containing 23.05 mg (0.05 mmoles) of Dig-CM0, 50.35 mg (0.1 mmoles) fluorescein-LC-NH$_2$ and 19.2 mg (0.1 mmoles) EDAC in 1.5 mL of DMF/DMSO (5:1) solvent was stirred overnight at room temperature in the dark. The Dig-LC-F and Dig-CMO were precipitated out by adding 3 mL of D-H$_2$O, filtered, and the solvent discarded. The filtered material was resolubilized in a solvent system consisting of CH$_2$CH$_2$:methanol:acetic acid=60:40:5 and was loaded onto a (1.5×20 cm) silica gel column in the same solvent system. Under these conditions, Dig-CMO moved ahead of Dig-LC-F conjugate, and the F-LC-NH$_2$ remained bound to the top of the column. The purity of the material was checked by TLC silica gel plates, using the solvent system described above, and by electrophoresis on paper at pH=5.8. The solvents were removed from the purified material by rotoevaporation under reduced pressure, the product was resolubilized into a minimum volume of methanol/DMF (70:30) and centrifuged to remove any unsoluble materials (silica gel). The last step was performed to remove most of the silica gel, which may be solubilized and co-eluted with the product during the purification. The product was stored in methanol/DMF (70:30) solvent system at −10° C. to −20° C. The concentration of the product was determined by $A_{490}$ from a standard curve constructed using known amounts of 6-carboxyfluorescein.

D. Preparation of Anti-Fluorescein-HRP Conjugate

The anti-fluorescein antibodies used were monoclonal anti-fluorescein antibodies prepared using standard monoclonal antibody techniques (Milstein, C. and Kohler, G., *Nature* 256:495 (1975)). Before conjugation to HRP, these antibodies were purified to IgG fraction by immobilized Protein A or by Ab$_x$ matrix (combined with a sizing column of Sephacryl S-200). The working pH range for the latter was 5.8–7.0.

1. Preparation Of HRP-NHS. Succinylated HRP (HRP-COOH) was used for the preparation of the conjugate. To the 1.25 mL of 20 mg/mL HRP-COOH in 0.003 M NaPi/pH=6.9, 13 mg of sulfo-NHS was added. After adjusting the pH of the mixture back to 6.9 by 0.2 M Na$_2$HPO$_4$, 20 mg EDAC was added. The reaction mixture was incubated for 20 minutes at room temperature and then purified on a Sephadex G-25 column in PBS/pH=7.1. The purified HRP-NHS was immediately used for conjugation with fluorescein antibody (Ab$_F$).

2. Preparation of anti-fluorescein-HRP conjugate (Ab$_F$-HRP).

Before conjugating, the fluorescein antibody was dialyzed against 0.02 M NaPi, 0.14 M NaCl/pH=7.2, and then $F_{520}$ was added to a final concentration equal to that of the binding sites. ($F_{520}$ was used to block the binding sites of the anti-fluorescein antibody.

To 0.9 mL of 20 mg/mL HRP-NHS was added 3 mL of 2 mg/mL Ab $_{F520}$ in PBS/pH7.2 and the mixture incubated at 4° C. for 4.5 hours (if the mixture is concentrated in the beginning, the efficiency of the conjugation chemistry will improve, but care should be taken to minimize the aggregate formation). The reaction was stopped by adding hydroxyl amine to a final concentration of 0.1 M in reaction mixture (pH=7.0) and incubated overnight at 4° C. The reaction mixture was concentrated to approximately 2 mL using an Amicon concentrating device with YM-10 membrane, then purified on a Sephacryl S-300 column (1.5×114 cm). The peak material corresponding to MW=200K–250K was used in the assays.

E. Preparation of Avidin-Glass Beads (GB)

Glass beads of approximately 0.75 mm in diameter (Glen Mills, Inc., Maywood, N.J.) were first cleaned by boiling in 5% nitric acid for one hour and then washed with deionized water until the wash was neutral in pH. The beads were dried at room temperature under vacuum.

To 1 kg of the acid-washed beads was added 1 mL of aminopropyltriethoxysilane in 300 mL ethyl acetate. The mixture was then placed on a rotary aspirator, and upon removal of the solvent, the beads were coated with a thin film of the aminosilane reagent. The beads were then transferred to a stainless reactor and heated in an oven at 130° C. overnight under nitrogen/argon atmosphere. After cooling, the beads were used directly in the next step.

To 500 g of the aminated beads in a canted tissue culture flask was added 170 mL 0.1 M of sodium borate pH 9.0 for 10 minutes. A solution of succinic anhydride (2.0 g in 20 mL DMF) was added by pipette. The flask was capped and shaken manually. All liquid was removed upon the final addition of succinic anhydride solution, and the beads were washed with deionized water 200 mL×4.

After flushing once with 150 mL 0.1 M MES (2-[N-morpholino]ethanesulfonic acid), pH 5.2, the beads were resuspended in MES to the liquid volume to just cover the beads. One hundred milligrams (100 mg) of EDAC (1-ethyl-3-[3-dimethylaminopropyl]carbodiimide) in 2 mL MES was added in one portion and mixed for 5 minutes with manual shaking. Upon removal of the liquid by use of an aspirator, a 20 mL MES solution of avidin (20 mg) and BSA (40 mg) was added in one portion. The beads were mixed manually and more MES buffer was added to just cover the beads. Finally, the culture flask with its contents was placed on an orbital shaker overnight at 4° C.

Further preparation of the beads includes washing the beads with 1 N NaCl (200 mL×4) followed by deionized water (200 mL×4). Before and after each wash, the liquid is removed entirely. The beads are then treated with a phosphate-saline buffer (20 mM phosphate, 140 mM NaCl 0.02% NaN$_3$, pH 7.4) containing 0.1% BSA and 2.5% sucrose (150 mL×3). Excess liquid is removed and the wet beads are transferred to a container in a vacuum dessicator.

Finally, after passage through a number 16 or 20 USA Standard Testing Sieve, the beads were dusted with casein powder to prevent sticking together upon storage.

Binding study with $^3$H-biotin indicated that the beads thus prepared incorporated 2–11 μg active avidin/g beads.

F. TMB/H$_2$O$_2$ HRP Substrate

Concentrated stock solutions of TMB and urea hydrogen peroxide were prepared separately and stored frozen. Fresh working substrate solution was prepared each time by diluting and mixing the two reagents together. The concentrated stock solutions were prepared as follows:

TMB stock solution (Solution 1)

6.82 g Citric Acid (MW=192.1 )

0.652 g TMB×2HCl (MW=313.3)

Dissolve in 100 mL of D-H$_2$O.

Urea hydrogen peroxide stock solution (Solution 2 )

5 g Na$_3$ Citrate×2 H$_2$O (MW=294.1)

0.372 g EDTA (Na$_4$) (MW=380.2)

0.752 g Urea H$_2$O$_2$ (MW=94.07)

Dissolve in 100 mL of D-H$_2$O.

Preparation of the substrate working solution 8 mL of 0.125 M NaH$_2$PO$_4$ 1 mL of Solution 1

1 mL of Solution 2

After mixing, it was used immediately.
Assay Protocol

The protocol of the digoxin assay consists of three parts: 1.) the binding reaction between assay components (biotin-$Ab_{Dig}$+Dig-LC-F+$Ab_F$-HRP) in solution phase to form the complex (biotin-$Ab_{Dig}$--Dig-LC-F--$Ab_F$-HRP); 2.) the binding and separation of the complex from the unbound assay components by GB-Avidin; and 3.) addition of enzyme substrate and color generation.

The digoxin assay was performed in 10×75 mm disposable glass tubes by the sequential addition of 50 µl of the standard in normal human pooled serum or the unknown sample, 50µl of 1.74 ng/ml Dig-LC-F in assay buffer (0.2 M NaPi, 0.14 M NaCl and 0.1% BSA to pH 7.4) and 100 µl of a mixture of 80 ng/ml biotin-$Ab_{Dig}$ and 1 µg/ml $Ab_F$-HRP conjugate. The assay mixtures were agitated in a vortex mixer and incubated at 37° C. for 10 minutes. After incubation, the separation of bound signal generator ($Ab_F$-HRP from unbound was performed by addition of 0.65 g of GB-avidin into each tube, then incubating 10 minutes at 37° C. and finally washing with 4×1 ml of wash buffer (0.01 M NaPi,pH 7.2). After washing, 0.3 ml of HRP substrate (TMB/urea $H_2O_2$) per tube was added and incubated at 37° C. for 5 minutes. Using a standard curve, constructed with the method described, thirty-nine patient samples were quantitated for digoxin concentration. The results obtained compared favorably with values generated by known radioimmune assays (RIAs).

EXAMPLE 2

Heterogeneous enzyme-based immunoassay for total $T_3$
Preparation Of Materials
A. Preparation Of $T_3$-LC-F Conjugate The reagent was prepared in three successive steps by preparing (1)F-NHS, (2) F-LC-$NH_2$, and (3) $T_3$-LC-F. The F-NHS and F-LC-$NH_2$ were prepared as described in Example 1.

A solution, containing 30.4 mg (0.05 mmoles) of triiodothyroformic acid, 50.35 mg (0.1 mmoles) F-LC-$NH_2$ and 19,2 mg (0.1 mmoles) EDAC in 1 mL of DMF/DMSO (4:1) solvent, was stirred overnight at room temperature in the dark. The $T_3$-LC-F and triiodothyroformic acid (if any left unreacted) were precipitated by adding 5 mL of D-$H_2O$, filtered, and the solvent discarded. The filtered material was resolubilized in a solvent system consisting of $CH_2Cl_2$:methanol: acetic acid (50:50:5) and was loaded onto a 1.5×20 cm silica gel column in the same solvent system. Under these conditions, triiodothyroformic acid moved ahead of $T_3$-LC-F conjugate, and the F-LC-$NH_2$ remained bound to the top of the column. The purity of the material was checked by TLC silica gel plates, using the solvent system described above. The solvents were removed from the purified material by rotary evaporation and the product was resolubilized into a minimum volume of methanol/DMF (70:30). The last step was performed to remove most of the silica gel, which may be solubilized and co-eluted with the product during the purification. The product was stored in methanol/DMF (70:30) solvent system at −20° C. The concentration of $T_3$-LC-F in the stock solution was determined by $A_{490}$ from a standard curve constructed using known amounts of 6-carboxy-fluorescein.

B. Preparation of Ab$T_3$-Biotin

Anti-$T_3$ antibodies were purified to the IgG fraction using immobilized Protein A. The antibody IgG's were biotinylated using biotin-LC-NHS (Ab:biotin-LC-NHS= 1:25 molar ratio in the reaction mixture). The uncoupled biotin was removed by Sephadex-G25 column, and the $Ab_{T3}$-biotins were stored in 0.05 M NaPi/pH=7.4 at 4° C. or frozen.

C. Coupling the Avidin to Glass Beads (GB)

The reagent was prepared by modifying the 0.5 mm–1.0 mm nonporous glass beads with 3-aminopropyltriethoxysilane to generate reactive amino groups on the surface of glass beads. The GB-$NH_2$ then was coated with CM-dextran using EDAC and finally succinylated to convert all of the amino groups into carboxyl groups. Avidin was coupled to the CM-dextran coated GB by EDAC chemistry. Finally, the avidin-labeled glass beads were coated with a solution containing 2.5% sucrose, 0.1% BSA. After drying the beads under reduced pressure, they were used in the assays.

Example 1 provides an alternative method for preparing the avidin coated glass beads.

D. Assay Working Solutions

1. Assay Buffer. 0.075 M Sodium barbital, 0.2 M NaCl, 0.002% thimerosal, 0.1% BSA, pH=8.6.
2. Releasing Reagent (RR). Assay buffer containing 1 mg/mL ANS, 5 mM EDTA, 0.5 mg/mL BGG, 0.5 mg/mL sheep IgG, 4% normal mouse serum was used to release the bound $T_3$ from serum proteins.
3. TMB/$H_2O_2$ HRP Substrate. Concentrated stock solutions were prepared as described in Example 1.

Assay Protocol

The assay was performed in 10×75 mm disposable glass tubes by the sequential addition of 50 µl of the commercially available standard or the unknown serum sample, 50 µl of 1.5 ng/ml $T_3$-LC-F in the releasing reagent, and 100 µl of a mixture of 80 ng/ml biotin-$Ab_{T3}$ and 1 µg/ml $Ab_F$-HRP conjugates. The assay mixtures were agitated in a vortex mixer and incubated at 37° C. for 15 minutes. After incubation, the separation of bound signal generator ($Ab_F$-HRP) from unbound was performed by the addition of 0.65 g of GB-avidin into each tube, incubating for 10 minutes at 37° C., and washing with 4×1 ml of wash buffer (0.01 M NaPi, pH 7.2). After washing, 0.3 ml of HRP substrate (TMB/urea $H_2O$) per tube was added and incubated at 37° C. for 5 minutes. The reaction was stopped by adding 1 ml of 1N $H_3PO_4$ and the amount of color generated was measured at $A_{450}$. Using the standard curve, constructed using the method described above, 41 patient serum samples were quantitated for $T_3$ concentrations. The results obtained compared favorably with values generated by known radioimmune assays (RIAs).

EXAMPLE 3

Heterogeneous enzyme-based immunoassay for detection of TSH
Preparation of materials
A. Preparation of $Ab_{TSHB}$#1—Biotin Anti-TSH antibodies were either purified by immobilized Protein A to obtain the Ab IgG fraction or purchased pure from a commercial source. (BiosPacific, Menlo Park, Calif.; Cambridge Medical, Cambridge, Mass.). The Ab-biotin was prepared by mixing the Ab (1–3 mg/ml) in 0.1M NaPi, 0.2 m Nacl/$p_H$ 7.5) and sulfo-NHS-LC-Biotin. The sulfo-NHS-LC-Biotin was added in 3–5 aliquots over fifteen minutes and the reaction was allowed to run at room temperature for 1.5 hr. Uncoupled biotinylating reagent was removed by a Sephadex G-25 column. The molar ratio of Ab:Sulfo-NHS-LC-Biotin was 1:10, 1:20 and 1:40. The conjugate was stored in reaction buffer containing 0.001% thimerisol.

B. Preparation of $Ab_{TSHB}$#2—F1

1. Preparation of F-NHS; To 3.4ml DMF containing 377.12 mg 6-carboxyfluorescein and 115 mg NHS was added 0.6 ml DMF containing 206.3 mg DCC. The mixture was stirred, overnight at room temperature. Dicycloxexylurea was removed by filtration. The F-NHS was checked by TLC on silica plates using dichloromethame:methanol:acetic acid=90:10:1. F-NHS was stored in DMF at −20° C.

2. Preparation of $Ab_{TSH\beta}$—F: Anti-TSH was purified by Protein A chromatography and dialyzed into 0.1M NaPi, 0.2 m NaCl, 5 mM EDTA pH 7.3. The Ab-F was prepared by mixing the Ab (1.5–2.0 mg/ml) with F-NHS in DMF and allowing the reaction to run for 1.5 hr. at room temperature. F-NHS:Ab ratios used were 12.5:1 and 25:1.

C. Preparation of the anti-fluorescein—HRP conjugate

Reagent was prepared as described in Example 1

D. Assay Protocol

The protocol of the TSH assay consists of three parts: 1.) the binding reaction between assay components (biotin $Ab_{TSH1}$, TSH, $A_{TSH2}$-F and $Ab_F$-HRP) in solution phase; 2.) the separation of the complex from the unbound assay components by GB-Avidin; and 3.) addition of enzyme substrate and color generation.

The TSH assay is performed in 10×75 mm glass tubes. To 150 µl of human or bovine serum containing various amounts of TSH is added 20 µl buffer (0.01M NaPi 0.150 M NaCl, 1.0% BSA, 0.1% Tween-20) containing 200 ng $Ab_F$-HRP and 20 µl buffer containing 180 ng $Ab_{TSH1}$-biotin and $Ab_{TSH2}$-F. The assay tubes were agitated on a vortex mixer and incubated at 37° C. for 12.5 minutes. After incubation 0.65 g GB-avidin was added and incubation was allowed to continue for an additional 12.5 minutes. The beads were then washed 4 times with 1.0 ml of wash buffer (0.01M NaPi, 0.15 M NaCl, 0.1% Tween, pH 7.4). After washing 0.2 ml of HRP substrates (TMB/$H_2O_2$) was added and color allowed to develop for 5 minutes. The reaction was stopped by the addition of 0.4 ml $H_3PO_4$. Samples were diluted to 1.0 ml total volume and the optical density at $OD_{450}$ was measured.

The above description and examples serve to fully disclose the mixture including preferred embodiments thereof. Modifications obvious to those of ordinary skill in the art are intended to be within the scope of the following claims.

What is claimed is:

1. A composition of matter consisting of a conjugate of a monoepitopic antigen covalently bound to a small molecule, said conjugate being bound in a termolecular complex with antibody for said monoepitopic antigen and an antibody for said small molecule, wherein said small molecule is an organic or organometallic group having a molecular weight of from 100 to 2000 and for which a receptor exists or can be prepared.

2. The composition of matter of claim 1 wherein said antigen and said small molecule are connected by a chain of at least 10 atoms in length.

3. The composition of claim 1 wherein one antibody is bound to a label.

4. The composition of claim 3 wherein said label is an enzyme, chemiluminescer or fluorophore.

5. The composition of claim 3 wherein the other antibody is covalently bound to a second small molecule, wherein said small molecule is an organic or organometallic group having a molecular weight of from 100 to 2000 and for which a receptor exists or can be prepared.

6. The composition of claim 5 wherein said second small molecule is bound to a support having a receptor for said second small molecule.

7. A composition of matter $E\text{-}Ab_F\text{:}F\text{-hapten:}Ab_{hapten}\text{-}X\text{: }Y\text{-support}$ where $E\text{-}Ab_F$ is an anti-fluorescein antibody bound to an enzyme; F-hapten is a fluorescein bound hapten; $Ab_{hapten}\text{-}X$ is an anti-hapten antibody bound to biotin; and Y-support is avidin bound to a support.

8. A composition of matter $E\text{-}Ab_F\text{:}F\text{-}Ab_1\text{:}A\text{:}Ab_2\text{-}X\text{:}Y\text{-support}$ where $E\text{-}Ab_F$ is an anti-fluorescein antibody bound to an enzyme; $F\text{-}Ab_1$ is a fluorescein bound first antibody; A is a multiepitopic antigen; $Ab_2\text{-}X$ is a second antibody bound to biotin; and Y-support is avidin bound to a support.

9. A composition of matter $E\text{-}Ab_F\text{:}F\text{-}Ag\text{:}Ab\text{:}Ab\text{-}X\text{:}Y\text{-support}$ where $E\text{-}Ab_F$ is an anti-fluorescein first antibody bound to an enzyme; F-Ag is a fluorescein bound antigen; Ab is a second antibody complementary to said antigen; Ab-X is a third antibody complementary to said second antibody bound to biotin; and Y-support is avidin bound to a support.

10. A composition of matter $E\text{-}Ab_F\text{:}F\text{-}Ab\text{:}Ab\text{:}Ag\text{-}X\text{: }Y\text{-support}$ where $E\text{-}Ab_F$ is an anti-fluorescein first antibody bound to an enzyme; F-Ab is a fluorescein bound antibody; Ab is a second antibody; Ag-X is an antigen complementary to said second antibody bound to biotin; and Y-support is avidin bound to a support.

11. A composition of matter $E\text{-}Ab_F\text{:}F\text{-}Ab_1\text{:}A\text{:}Ab_2\text{-}X$ where $E\text{-}Ab_F$ is an anti-F antibody bound to an enzyme, where F is a first small molecule; $F\text{-}Ab_1$ is said first small molecule (F) covalently bound to a first antibody; A is a multiepitopic antigen; and $Ab_2\text{-}X$ is a second antibody covalently bound to a second small molecule., wherein said small molecules are organic or organometallic groups having a molecular weight of from 100 to 2000 and for which a receptor exists or can be prepared.

12. The composition of matter of claim 11 wherein said first small molecule is a fluorescein derivative and said second small molecule is biotin.

* * * * *